United States Patent
Goossens et al.

(10) Patent No.: US 11,533,934 B2
(45) Date of Patent: Dec. 27, 2022

(54) ANIMAL FEED MATERIAL

(71) Applicant: NUTRIAD INTERNATIONAL NV, Turnhout (BE)

(72) Inventors: Tim Goossens, Dendermonde (BE); Filip Florimond Magdalena Van Immerseel, Dendermonde (BE); René Kwakkel, Dendermonde (BE); Pierre Clément Antoine Moquet, Dendermonde (BE); Lonneke Onrust, Dendermonde (BE)

(73) Assignee: NUTRIAD INTERNATIONAL, Turnhout (BE)

( * ) Notice: Subject to any disclaimer, the term of this patent is extended or adjusted under 35 U.S.C. 154(b) by 0 days.

(21) Appl. No.: 16/954,090

(22) PCT Filed: Dec. 20, 2018

(86) PCT No.: PCT/EP2018/086173
§ 371 (c)(1),
(2) Date: Jun. 15, 2020

(87) PCT Pub. No.: WO2019/122112
PCT Pub. Date: Jun. 27, 2019

(65) Prior Publication Data
US 2021/0186057 A1   Jun. 24, 2021

(30) Foreign Application Priority Data

Dec. 22, 2017   (BE) .................... 2017/5984

(51) Int. Cl.
| | |
|---|---|
| A23K 20/163 | (2016.01) |
| A23K 20/195 | (2016.01) |
| A23K 50/75 | (2016.01) |
| A61P 31/04 | (2006.01) |
| A61K 31/717 | (2006.01) |

(52) U.S. Cl.
CPC .......... *A23K 20/163* (2016.05); *A23K 20/195* (2016.05); *A23K 50/75* (2016.05); *A61K 31/717* (2013.01); *A61P 31/04* (2018.01)

(58) Field of Classification Search
CPC .... A23K 20/163; A23K 20/195; A23K 50/75; A61P 31/04; A61K 31/717
USPC ........................................................ 514/57
See application file for complete search history.

(56) References Cited

U.S. PATENT DOCUMENTS

| | | |
|---|---|---|
| 5,089,271 A | 2/1992 | Unangst |
| 2001/0020091 A1* | 9/2001 | Buchanan ............... C08B 11/00 536/123 |
| 2003/0175326 A1 | 9/2003 | Thombre |

FOREIGN PATENT DOCUMENTS

| | | |
|---|---|---|
| BE | 1023491 A1 | 10/2015 |
| EP | 1354520 A1 | 4/2003 |
| GB | 2466041 A | 6/2010 |
| NO | 2007124949 A1 | 11/2007 |
| WO | 2016055651 A1 | 4/2016 |
| WO | 2018174141 A1 | 9/2018 |

OTHER PUBLICATIONS

Glossary of medical education terms, Institute of International Medical Education. http://www.iime.org/glossary.htm Accessed in Mar. 2013. (Year: 2013).*

M'Sadeq et al. Dietary acylated starch improves performance and gut health in necrotic enteritis challenged broilers. Poultry Science 94:2434-2444, 2015. (Year: 2015).*

F. Van Immerseel et al. "Supplementation of Coated Butyric Acid in the Feed Reduces Colonization and Shedding of *Salmonella* in Poultry", Poultry Science Association, Inc., Jun. 9, 2005, vol. 84, pp. 1851-1856.

International Search Report dated Jan. 31, 2019 re: Application No. PCT/Ep2018/086173, pp. 1-4, citing: Li Mufang et al. Highly hydrophilic . . . ), US 2003/175326 A1, US 5 089 271 A, WO 2007/124949 A1, GB 2 466 041 A, WO 2016/055651 A1 and WO 2018/174141 A1.

Mufang Li et al. "Highly hydrophilic and anti-fouling cellulose thin film composite membrane based on the hierarchical poly(vinyl alcohol-co-ethylene_nanofiber substrate", Cellulose Springer Netherlands, Jun. 16, 2015, vol. 22, No. 4, pp. 2717-2727 XP035515892.
Written Opinion dated Jan. 31, 2019 re: Application No. PCT/Ep2018/086173, pp. 1-9, citing: Li Mufang et al. Highly hydrophilic . . . ), US 2003/175326 A1, US 5 089 271 A, WO 2007/124949 A1, GB 2 466 041 A, WO 2016/055651 A1 and WO 2018/174141 A1.

* cited by examiner

*Primary Examiner* — Yih-Horng Shiao
(74) *Attorney, Agent, or Firm* — Cantor Colburn LLP

(57) ABSTRACT

A feed material for livestock is effective in prevention and/or treatment of pathogenic infections in livestock and/or in increasing efficiency in livestock production.

Enteral administration of polysaccharide butyryl esters to livestock animals results in increased butyrate concentrations in the lower intestinal tract. This leads amongst others to a reduced presence of pathogens in the lower intestinal tract and feces and superior growth performance results compared to other butyrate formulations or products. The feed material provides polysaccharide butyryl esters, compositions, such as feed additives and/or feed, having the polysaccharide butyryl esters, as well as the uses of the polysaccharide butyryl esters as feed additive, e.g. for preventing or treating pathogenic infections in livestock and/or in increasing efficiency in livestock production.

6 Claims, 4 Drawing Sheets

ANIMAL FEED MATERIAL

TECHNICAL FIELD

The present disclosure relates to the field of livestock animal feed, in particular to a feed material that is effective in prevention and/or treatment of pathogenic infections in livestock and/or in increasing efficiency in livestock production.

BACKGROUND

The growing demand for livestock products worldwide requires novel strategies that increase the efficiency of livestock production. Optimization of nutrient utilization is an essential element in such strategies. Consumer and governmental focus on food safety, lowering environmental impact, better animal welfare and prudent antimicrobial use generate additional demands on livestock production.

One particular area of attention in livestock production is the eradication of pathogens, such as *Salmonella* and other pathogenic bacteria. *Salmonella* is one of the most important causes of foodborne infections in humans, mainly due to the consumption of poultry meat or contaminated eggs. The agricultural sector attempts to reduce the number of *Salmonella* infections by different measures such as vaccination, intensive hygienic measures and/or administration of antibiotics, probiotics, acidifiers, or short- and medium-chain fatty acids and salts thereof.

Recently, the bacteriostatic effects of volatile short-chain fatty acids on gram-negative bacteria have attracted attention. The group of volatile short-chain fatty acids consists of biodegradable weak organic acids that are able to eliminate pathogenic microorganisms without significantly affecting the intestinal microflora. It has been shown that volatile short-chain fatty acids may inhibit the growth of *Escherichia coli* hemolytic strains by 50 percent. A number of short chain fatty acid compositions have been developed for use as a feed additive in order to achieve reductions of pathogens in animals.

EP1354520 describes a feed additive which is a microcapsule comprising n-butyric acid in a matrix comprising a lipidic structure (wax) and its preparation by spray-cooling. According to EP1354520 micro-encapsulation of butyric acid is useful in particular to counteract the difficulties associated with the volatility and rancid smell of butyric acid, which create difficulties in the handling as a feed additive. It is also suggested in EP1354520 that the formulation is stable against gastric degradation.

F. Van Immerseel et al. (2005 Poultry Science 84: 1851-1856) compared the effect of butyric acid with butyric acid embedded in a fat matrix when used as a feed additive for poultry. They reported that colonization of caeca by *Salmonella* and fecal shedding of *Salmonella* was significantly lower in the group which was administered butyric acid embedded in a fat matrix.

WO2007/124949 describes the use of 3-hydroxybutyric acid and poly-3-hydroxybutyric acid compounds as feed additives.

BE1023491 describes a feed additive comprising butyric acid in a wax matrix comprising microcrystalline wax, and its production by melt extrusion.

The present disclosure provides animal feed additives possessing improved effectiveness in preventing or treating pathogenic infections in livestock and/or in increasing efficiency in livestock production.

SUMMARY

The present inventors have surprisingly found that these objectives can be met with certain esters of polysaccharide and butyric acid.

It has been found that enteral administration of polysaccharide butyryl esters of the present disclosure to livestock animals results in increased butyrate concentrations in the lower intestinal tract. The present inventors assume this correlates to the effectiveness of the polysaccharide butyryl esters on pathogenic presence in the lower intestinal tract and feces that has been observed during in vivo trials. It was also surprisingly found that administration of the polysaccharide butyryl esters resulted in superior growth performance results compared to other butyrate formulations or products. The polysaccharide butyryl esters in accordance with the present disclosure provide the highly desirable combination of improved average daily weight gain (ADG) and average daily food intake (ADFI) combined with decreased feed conversion ratio (FCR) and mortality during the supplementation period without showing adverse effects during the finisher period.

Butyric acid is presumed to stimulate the growth of the intestinal villi and/or modifies the development of gastroenteric micro-organisms. It is also believed that butyric acid can downregulate expression of genes involved in *Salmonella* invasion at low doses. Other beneficial effects which the inventors envisage upon use of the polysaccharide butyryl compositions of the present disclosure may comprise an improved retention of intestinal content in the small intestine, an improved digestion/absorption of methionine and/or a more diverse microbial population in the lower gastro-intestinal tract.

The origin of the butyric acid concentration increase may be a prebiotic effect (for example, but not limited to a prebiotic effect on butyric acid producing bacteria), direct release of butyric acid resulting from degradation of the polysaccharide butyryl ester, any other mechanism resulting in a butyric acid concentration increase or a combination thereof. Without wishing to be bound by any theory, the present inventors believe that the effects observed for the polysaccharide butyryl esters of the present disclosure may also correlate with an increased presence of microorganisms capable of polysaccharide fermentation in the lower gastro-intestinal tract compared to the upper gastro-intestinal tract.

Hence the present disclosure provides novel polysaccharide butyryl esters, compositions, such as feed additives and/or feed, comprising the polysaccharide butyryl esters, as well as the uses of the polysaccharide butyryl esters as feed additive, e.g. for preventing or treating pathogenic infections in livestock and/or in increasing efficiency in livestock production.

These and other aspects of the disclosure will become apparent on the basis of the detailed description and the appended examples.

DETAILED DESCRIPTION

Figure 1:
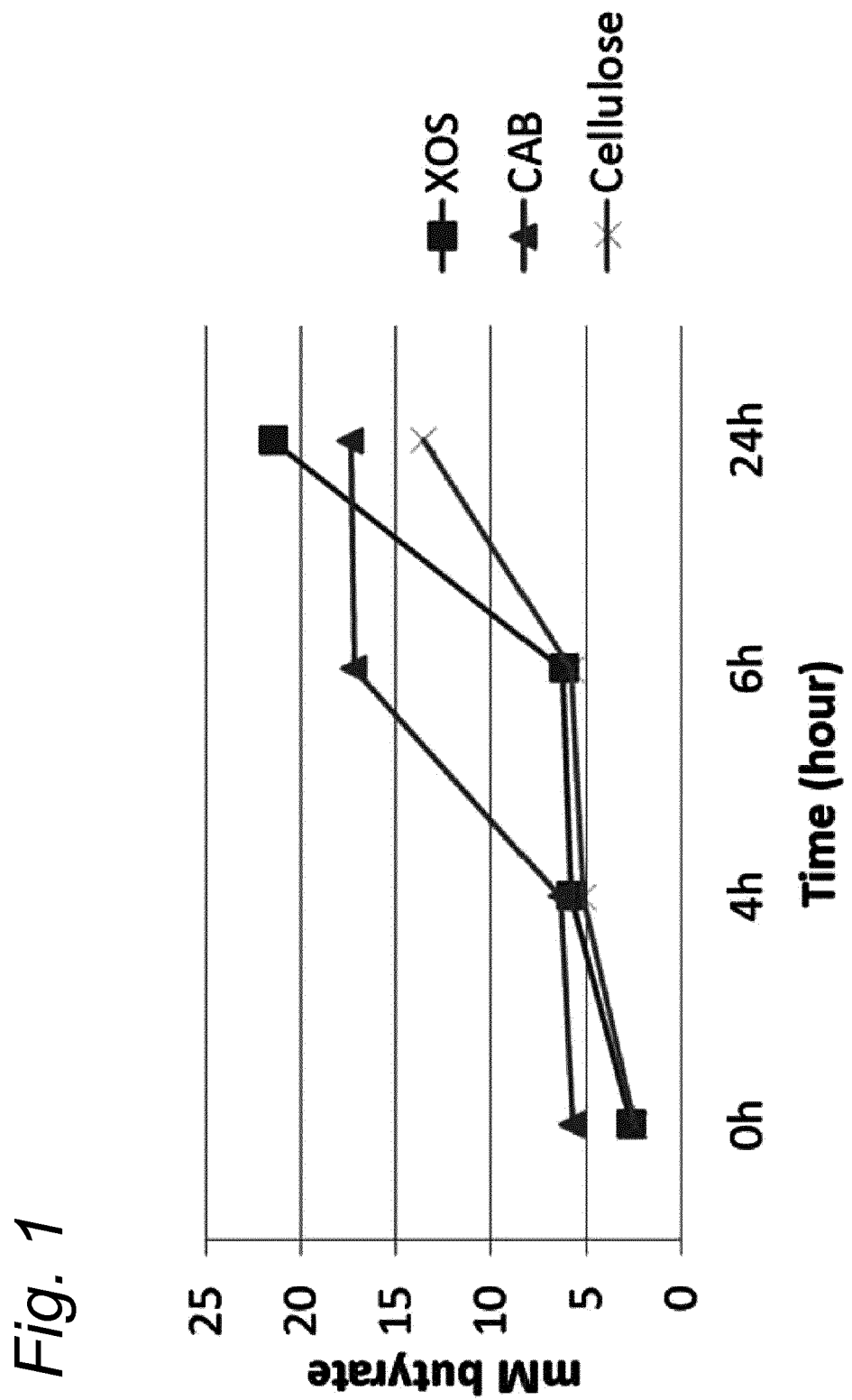
FIG. 1: Butyrate concentrations measured in example 1—Ileum inoculum.

A first aspect of the disclosure concerns a feed grade composition comprising a polysaccharide butyryl ester.

Butyric acid is a volatile short-chain fatty monocarboxylic acid having the molecular formula $CH_3$—$CH_2$—$CH_2$—COOH. The terms "butyric acid" and "butyrate" as used herein are used interchangeably and should be construed to denote the protonated (acid, butyric acid) and deprotonated (conjugate base, butyrate) forms respectively. The skilled person will understand that butyric acid, as it is a weak acid, is normally present in both protonated and deprotonated form when dissolved in an aqueous medium, the concentration of each form depending on the pH of the medium. The acid form can be absorbed by the intestinal walls and by the cellular membranes of micro-organisms.

As used herein, the term "polysaccharide butyryl ester" refers to compounds that, generally stated, comprise a polysaccharide molecule as the central portion, which polysaccharide molecule is derivatized/substituted with a plurality of butyric acid molecules through the formation of ester linkages between the carboxylic acid moiety of the butyric acid molecule and a hydroxyl group of the polysaccharide.

As used herein, the term "polysaccharide" refers to polymers comprising a backbone comprising monosaccharide repeating units and/or derivatized monosaccharide repeating units, typically cyclic pentoses, in particular $C_5$ aldoses or ketoses, or cyclic hexoses, in particular $C_8$ aldoses or ketoses. Non limiting examples of $C_5$-$C_8$ aldoses include allose, altrose, glucose, mannose, gulose, idose, galactose, talose, ribose, arabinose, xylose, lyxose. Non limiting examples of $C_5$-$C_8$ ketoses include ribulose, xylulose, fructose, sorbose and tagatose. As used herein, the term "monosaccharide derivatives" refers to any chemically or enzymatically modified monosaccharide unit.

The polysaccharide may be a homopolysaccharide or heteropolysaccharide, preferably a homopolysaccharide.

The polysaccharide may be a modified or unmodified. In a preferred embodiment of the disclosure a polysaccharide butyryl ester is provided, wherein the polysaccharide is selected from the group consisting of starches, modified starches, amylopectin, modified amylopectin, amylose, modified amylose, chitosan, chitin, guar gum, modified guar gum, locust bean gum, tara gum, konjac gum, konjac flour, fenugreek gum, mesquite gum, aloe mannans, modified cellulose, oxidized polysaccharides, sulfated polysaccharides, cationic polysaccharides, arabic gum, karaya gum, xanthan, kappa, iota or lambda carrageenans, agar-agar, alginates, callose, laminarin, chrysolaminarin, xylan, mannan, galactomannan, hemicellulose, pectin, arabinoxylan, xanthan gum, nigeran, isolichenan, laminaran, lichenan, glycogen, pullulan, dextran, pustulan, inulin, grass levans, carrageenan, galactocarolose, rhodymenan, fucoidan, agarose, porphyran, alginic acid, keratosulphate, chondroitin, chrondroitin sulphates, heparin and cellulose, preferably from the group consisting of hemicellulose, starch and cellulose, most preferably the polysaccharide is cellulose.

In a preferred embodiment of the disclosure a polysaccharide butyryl ester is provided, wherein the polysaccharide is selected from the group consisting of water insoluble polysaccharides.

For the purposes of the present disclosure, the polysaccharide butyryl ester may be formed chemically, enzymatically, fermentatively, through biosynthesis by a natural or genetically modified organism, etc. Typically, in accordance with the disclosure, the polysaccharide butyryl ester is produced by esterification of a polysaccharide such as acid-catalyzed esterification.

The amount of substituent groups on the (anhydro) monosaccharide units of polysaccharides can be designated by weight percent or by the average number of substituent groups attached to the ring, a concept known to polysaccharide chemists as "degree of substitution" (D.S.). In case of a $C_6$ monosaccharide, if all three available positions on each unit are substituted, the D.S. is designated as 3; if an average of two on each ring are substituted, the D.S. is designated as 2, etc. In analogy the amount of substituent groups on the polysaccharides can be can be expressed as a percentage of the available positions that are substituted.

In one embodiment of the disclosure, the polysaccharide butyryl ester has an average number of butyryl groups per monosaccharide unit (D.S.) within the range of 0.1-4. For example, in accordance with said embodiment, the D.S. may be at least 0.25, at least 0.5, at least 0.75, at least 1.0, at least 1.25, at least 1.5, at least 1.75, at least 2.0, at least 2.25 or at least 2.5 and/or it may be less than 3.75, less than 3.5, less than 3.25, or less than 3. In exemplary embodiments said D.S. is within the range of 0.5-3.5, within the range of 1.0-3.25, within the range of 1.5-3, or within the range of 2.0-2.95.

In a particularly preferred embodiment of the disclosure, the polysaccharide butyryl ester is a cellulose butyryl ester having an average number of butyryl groups per monosaccharide unit (D.S.) within the range of 0.1-4, preferably 1-3.5, preferably 1.75-3.25, preferably 2.25-3, preferably 2.5-2.95.

In other embodiments, the polysaccharide butyryl ester has a butyryl content of at least 5 wt. % by weight of the polysaccharide butyryl ester, preferably at least 10 wt. %, at least 15 wt. %, at least 20 wt. %, at least 25 wt. %, at least 30 wt. %, at least 35 wt. %, at least 40 wt. %, at least 45 wt. %, at least 50 wt. % or at least 55 wt. %. In embodiments of the disclosure, the polysaccharide butyryl ester is a cellulose butyryl ester characterized by a butyryl content within the range of 5-80 wt. % by weight of the polysaccharide butyryl ester, preferably 25-70 wt. %, 40-60 wt. %, or 50-56 wt. %.

In other embodiments, the polysaccharide butyryl ester has a butyryl content, expressed as the percentage of the available polysaccharide hydroxyl groups that is substituted, of at least 5%, preferably at least 10%, at least 15%, at least 20%, at least 25%, at least 25%, at least 30%, at least 35%, at least 40%, at least 45%, at least 50% or at least 55%. In other embodiments, the polysaccharide butyryl ester has a butyryl content resulting in a degree of substitution, expressed as the percentage of the available polysaccharide hydroxyl groups that is substituted, of 100% or less, e.g. less than 99%, less than 98%, less than 97%, less than 95%, less than 90%, less than 85%, less than 80%, or less than 75%.

In embodiments of the disclosure, the polysaccharide butyryl ester is a cellulose butyryl ester characterized by a butyryl content, expressed as the percentage of the available polysaccharide hydroxyl groups that is substituted, within the range of 5-80%, preferably 25-70%, 40-60%, or 50-56%.

In other preferred embodiments, the polysaccharide butyryl esters in accordance with the disclosure further comprise acetyl ester groups. In embodiments of the disclosure the polysaccharide butyryl ester comprises butyryl and acetyl groups in a molar ratio of at least 1/1, preferably at least 1.5/1, at least 2/1, at least 2.5/1, at least 3/1, at least 3.5/1, at least 4/1, at least 5/1, at least 6/1, at least 7/1, at least 8/1, at least 9/1 or at least 10/1. In embodiments of the disclosure the polysaccharide butyryl ester comprises butyryl and acetyl groups in a molar ratio of less than 100/1, preferably less than 75/1, less than 50/1, less than 40/1 less than 30/1 less than 25/1 less than 20/1 or less than 15/1. In embodiments of the disclosure the polysaccharide butyryl ester comprises acetyl groups and is characterized by an acetyl content of at least 1 wt. % by weight of the polysaccharide butyryl ester, preferably at least 2 wt. %, preferably at least 3 wt. %. In embodiments of the disclosure the polysaccharide butyryl ester comprises acetyl groups and is characterized by an acetyl content of at most 10 wt. % by weight of the polysaccharide butyryl ester, preferably at most 8 wt. %, preferably at most 5 wt. %.

In accordance with the disclosure, the polysaccharide butyryl ester is a cellulose butyryl ester characterized by an acetyl content in the range of 0.1-60 wt. % by weight of the cellulose butyryl ester, preferably 0.5-45 wt. %, preferably 1-30 wt. %, preferably 2-15 wt. %, preferably 3-10 wt. %, preferably 4-6 wt. %.

In embodiments of the disclosure, the polysaccharide butyryl ester may have a number average molar mass ($M_n$) in the range of 2,000-1,000,000 g/mol, preferably within the range of 5,000-500,000 g/mol, 7,000-250,000 g/mol, 10,000-100,000 g/mol, 12,000-50,000 g/mol, 13,000-25,000 g/mol, or 15,000-17,000 g/mol. In embodiments of the disclosure, the polysaccharide butyryl ester may be characterized by a number average molar mass ($M_n$) of at least 2,000 g/mol, preferably at least 4,000 g/mol, preferably at least 8,000 g/mol, preferably at least 12,000 g/mol. Furthermore, in embodiments of the disclosure, the polysaccharide butyryl ester may be characterized by a number average molar mass ($M_n$) of less than 1,000,000 g/mol, preferably less than 500,000 g/mol, preferably less than 250,000 g/mol, preferably less than 100,000 g/mol, preferably less than 70,000 g/mol, preferably less than 65,000 g/mol, preferably less than 30,000 g/mol, preferably less than 25,000 g/mol, preferably less than 17,000 g/mol. The number average molar mass ($M_n$) may be determined by suitable methods known to the person skilled in the art such as osmosis, static light scattering, sedimentation equilibrium, gel permeation chromatography, viscosimetry, sedimentation velocity, dynamic light scattering, end group analysis etc. A preferred method to determine the number average molar mass ($M_n$) is gel permeation chromatography.

In accordance with the disclosure, the composition comprising the polysaccharide butyryl ester is a feed grade composition. As used herein, the term "feed grade" means suitable for consumption by an animal, in particular livestock. In an embodiment it means that the composition has been determined to be safe, functional and suitable for its intended use in animal food. For example, it is handled and labeled appropriately, and/or conforms to the appropriate regulations governing the use of the composition in animal food in the relevant jurisdiction.

In embodiments of the disclosure, the feed grade composition comprises at least one further ingredient selected from the groups consisting of feed additives, feed grade formulating aids or excipients, and nutritional components.

It will be understood that the choice and the (relative) amounts of such additional ingredients will depend on the precise form and purpose of the feed grade composition. Embodiments are envisaged wherein the feed grade composition is a feed additive or feed material. Embodiments are also envisaged wherein the feed grade composition is a feed pre-mix or a feed or fodder that is ready to use. Unless indicated otherwise, the terms "feed additive" and "feed material" are used herein interchangeably, as generally referring to compositions that contain the polysaccharide butyryl ester in high concentrations, which compositions are designed and intended to be mixed with feed or fodder to provide the polysaccharide butyryl ester in adequate quantities/dosages. It is to be understood that these terms herein do not refer to legal definitions used in the context of animal feed regulations, which legal definitions may diverge among jurisdictions and/or change over time. Notwithstanding the former, it will be understood that the feed grade compositions of the disclosure can be provided in forms qualifying as a feed additive or feed material in the strict legal (i.e. regulatory) sense.

In embodiments of the disclosure, the feed grade composition is a feed material comprising the polysaccharide butyryl ester in association with at least one other feed grade material. In embodiments of the disclosure a feed material is provided comprising 0.1-80 wt. %, preferably 0.5-60 wt. %, 1-50 wt. %, 2-40 wt. %, 3-30 wt. %, 4-20 wt. %, 5-15 wt. % of the polysaccharide butyryl ester and one or more other feed grade materials.

In embodiments of the disclosure a feed material as defined herein is provided, wherein, said at least one other feed grade material is selected from the group of technological additives, sensory additives, nutritional additives, zootechnical additives, coccidiostats and histomonostats.

Examples of technological additives that can suitably be combined with the polysaccharide butyryl ester of the present disclosure include preservatives, antioxidants, emulsifiers, stabilisers, thickeners, gelling agents, binders, substances for control of radionucleotide contamination, anticaking agents, acidity regulators, silage additives and denaturants.

Examples of sensory additives that can suitably be combined with the polysaccharide butyryl ester of the present disclosure include colourants and flavoring compounds. Colourants should be construed broadly and may indicate substances that add or restore colour in feed, substances which when fed to animals add colours to food of animal origin and/or substances which favourably affect the colour of ornamental fish or birds.

Examples of nutritional additives that can suitably be combined with the polysaccharide butyryl ester of the present disclosure include vitamins, pro-vitamins and chemically well-defined substances having similar effect; compounds of trace elements; amino acids, their salts and analogues; urea and its derivatives.

Examples of zootechnical additives that can suitably be combined with the polysaccharide butyryl ester of the present disclosure include digestibility enhancers, gut flora stabilisers and substances which favourably affect the environment. In a preferred embodiment of the disclosure, the at least one other feed grade material comprised in the feed material is a binder, an anticaking agent, a stabilizing agent, a carrier and/or a preservative. In a preferred embodiment of the disclosure the at least one other feed grade material is selected from the group of a yeast product, a clay, a salt of a fatty acid, ilica, sepiolite, bentonite, clinoptilolite, guar gum, xantham gum, formic acid, sodium formate, calcium formate, acetic acid, calcium acetate, sodium propionate, calcium propionate, lactic acid, calcium lactate, Tocopherol-rich extracts from vegetable oils, and wheat bran. A yeast product as used herein should be construed broadly and may indicate yeast and its derivative products, such as inactivated dry yeast, yeast cell walls, autolysates, or nucleotides, obtained from e.g. *Saccharomyces cerevisiae, Saccharomyces carlsbergensis, Kluyveromyces lactis, Kluyveromyces fragilis, Torulaspora delbrueckii*, etc. In embodiments of the disclosure a feed material as defined herein before is provided, comprising the polysaccharide butyryl ester in an amount of up to 50 wt. %, based on the total weight of the composition, preferably up to 40 wt. %, up to 30 wt. %, up to 25 wt. %, up to 20 wt. %, up to 18 wt. %, up to 15 wt. %, up to 10 wt. %, or up to 5 wt. %.

In embodiments of the disclosure a feed material as defined herein is provided, comprising the one or more other feed grade materials, such as the feed grade material as defined here above, in a (combined) amount of at least 1 wt. %, based on the total weight of the composition, preferably at least 2 wt. %, at least 3 wt. %, at least 5 wt. %, at least 10 wt. %, at least 20 wt. %, at least 30 wt. %, at least 40 wt. %, or at least 50 wt. %.

In embodiments of the disclosure, the feed grade composition is a livestock feed, also referred to as fodder, comprising the polysaccharide butyryl ester as described herein and one or more animal feed ingredients. As is understood by those skilled in the art, the term "feed ingredient" as used herein refers to the feed components that provide the common nutrients needed for normal growth and development of the animal, the key nutrients being amino acids, carbohydrates, lipids, vitamins and minerals. Typically, feed ingredients are broadly classified into protein sources, energy sources, fat sources and mineral sources.

Thus, In embodiments of the disclosure a livestock feed as defined herein is provided, wherein the one or more feed ingredients are selected from the group of protein sources, energy sources, fat sources and mineral sources. Suitable examples of protein sources include soybean meal, rapeseed meal, palm kernel meal, sunflower meal, peas, beans, lupins, fish meal, poultry meal and blood plasma. Suitable examples of energy sources include corn, wheat, barley and rice. Suitable examples of fat sources include fish oil, tallow, corn oil, soy oil, rice bran oi, palm oil and canola oil. Suitable examples of mineral sources include calcium, magnesium, phosphorus, potassium, sodium, copper, selenium, zinc, iron, manganese, iodine, cobalt.

In embodiments of the disclosure a livestock feed as defined herein is provided, comprising the polysaccharide butyryl ester in an amount of at least 0.0001 wt. %, based on the total weight of the composition, preferably at least 0.001 wt. %, at least 0.005 wt. %, at least 0.01 wt. %, at least 0.025 wt. %, at least 0.05 wt. % or at least 0.1 wt. %. In embodiments of the disclosure a livestock feed as defined herein is provided, comprising the polysaccharide butyryl ester in an amount of up to 10 wt. %, based on the total weight of the composition, preferably up to 5 wt. %, up to 2 wt. %, up to 1 wt. %, up to 0.5 wt. % or up to 0.1 wt. %.

In embodiments of the disclosure, the feed grade composition has a free acid content of less than 5% by weight of the composition, preferably less than 2% by weight, preferably less than 1% by weight, preferably less than 0.5% by weight, preferably less than 0.1% by weight, preferably less than 0.05% by weight, preferably less than 0.01% by weight. The free acid content may be determined by suitable methods known to the person skilled in the art.

In embodiments of the disclosure, the feed grade composition has a water content of less than 5% by weight of the composition, preferably less than 2% by weight, preferably less than 1% by weight, preferably less than 0.5% by weight, preferably less than 0.1% by weight, preferably less than 0.05% by weight, preferably less than 0.01% by weight. The water content may be determined by suitable methods known to the person skilled in the art such as Karl-Fischer titration.

The feed grade compositions comprising a polysaccharide butyryl ester as described herein above, may be provided in powder, compacted, granulated or pelletized form. In preferred embodiments the polysaccharide butyryl ester is homogenously distributed throughout the feed grade composition.

In preferred embodiments the feed grade composition is provided in compacted, granulated or pelletized form and the polysaccharide butyryl ester is distributed throughout the primary particles making up the food grade composition.

In highly preferred embodiments the feed grade composition is provided in compacted, granulated or pelletized form wherein the primary particles making up the food grade composition do not comprise distinguishable layers or phases. In highly preferred embodiments the feed grade composition is provided in compacted, granulated or pelletized form wherein the primary particles making up the food grade composition which comprises polysaccharide butyryl ester do not comprise a coating consisting of or comprising the butyryl ester in amounts of more than 70%, more than 50% or more than 20 wt. % by total weight of the coating.

A second aspect of the present disclosure is directed to a method of treating an animal by administering a polysaccharide butyryl ester as defined herein. Typically, as will be understood on the basis of the foregoing, such methods involve enteral, in particular oral, administration of the polysaccharide butyryl ester to an animal, preferably in admixture with the animal's feed, with the purpose of affecting the animal's physiological state, in particular with the purpose of improving the animal's intestinal health, condition and/or performance. Methods of the present disclosure may thus have a prophylactic or curative effect. Methods of the present disclosure may also have a purely economic purpose.

In accordance with the disclosure, the animal is preferably a livestock animal, including avian species, aquatic species, and mammalian species. Examples of avian species include poultry species, such as turkey, duck and chicken. Examples of aquatic species include fish species, such salmon, trout, tilapia, catfish and carp, and crustacean species, including shrimp and prawn. Examples of mammalian species include ruminant species, such as sheep, goat, and cattle, and non-ruminant species, such as horses, pigs and swine. In a preferred embodiment of the disclosure, the animal is selected from the group consisting of monogastric animals with hindgut fermentation. In other preferred embodiments the animal is selected from the group consisting of chicken, pigs, horses, calves, goats, sheep, rabbits, dogs, cats and fish. In more preferred embodiments the animal is selected from the group consisting of chicken, pigs, horses calves, goat sheep and rabbits, more preferably from the group consisting of chicken, pigs, horses and calves, more preferably from the group consisting of chickens and pigs, most preferably chickens.

In embodiments of the disclosure, the animal to be treated can be an animal that is in the weaning period, an animal that is in the starter period, an animal that is in the grower period or an animal that is in the finisher period. In preferred embodiments, the animal is an animal that is in the starter period.

In embodiments of the disclosure, the method of treatment comprises feeding the animal a feed or fodder, typically a feed or fodder as defined herein elsewhere, comprising the polysaccharide butyryl ester. The optimal treatment regimen may depend on the species treated and/or the effect aimed at and, based on the present teachings, it will be within the capabilities of those skilled in the art to determine appropriate treatment regimens. In embodiments of the disclosure, the treatment will comprise the enteral, e.g. oral, administration of the polysaccharide butyryl ester in a dose of at least 0.0001 wt. %, based on the total weight of the animal feed consumed by the animal in 24 h, preferably at least 0.001 wt. %, at least 0.005 wt. %, at least 0.01 wt. %, at least 0.025 wt. %, at least 0.05 wt. % or at least 0.1 wt. %. In embodiments of the disclosure a treatment as defined herein is provided, comprising the enteral, e.g. oral administration of the polysaccharide butyryl ester in a dose of up to 10 wt. %, based on the total weight of the animal feed consumed by the animal in 24 h, preferably up to 5 wt. %, up to 2 wt. %, up to 1 wt. %, up to 0.5 wt. % or up to 0.1 wt. %.

In embodiments of the disclosure, the polysaccharide butyryl ester is administered in such doses at least once a week, preferably at least once every three days, more preferably at least once every two days, most preferably once a day.

The methods of the disclosure may be carried out for a variety of reasons, as will be evident on the basis of the foregoing, in particular for improving and/or maintaining the health of the animal and/or for improving the animal's performance.

Hence, in an embodiment of the disclosure, a method is provided as defined herein, wherein said method is non-therapeutic. Hence, a method is provided as defined herein, wherein the animal to be treated is an animal that is in good or normal health. In a preferred embodiment of the disclosure said method is aimed at decreasing the feed conversion ratio, increasing the life weight and/or increasing the average daily gain.

In embodiments of the disclosure, the method may be aimed at increasing the life weight at a given time, such as slaughter or day 35, preferably day 35, by more than 1%, preferably more than 2%, preferably more than 4%, preferably more than 6%. In a preferred embodiment the method is aimed at increasing the life weight at a given time by 1-12%, preferably 2-6%. The increase in life weight at a given time can be determined by the skilled person by routine experimentation, e.g. an in vivo experiment using a control group.

In embodiments of the disclosure, the method may be aimed at decreasing the feed conversion ratio, calculated over a given period, such as the supplementation period or lifetime, preferably the supplementation period, by more than 1%, preferably more than 2%, preferably more than 4%, preferably more than 6%. In a preferred embodiment the method is aimed at decreasing the feed conversion ratio calculated over a given period by 1-12%, preferably 2-6%. The decrease in the feed conversion ratio calculated over a given period can be determined by the skilled person by routine experimentation, e.g. an in vivo experiment using a control group.

In embodiments of the disclosure, the method may be aimed at increasing the average daily gain, calculated over a given period, such as the supplementation period or lifetime, preferably the supplementation period, by more than 1%, preferably more than 2%, preferably more than 4%, preferably more than 6%. In a preferred embodiment the method is aimed at increasing the average daily gain calculated over a given period by 1-12%, preferably 2-6%. The increase in the average daily gain calculated over a given period can be determined by the skilled person by routine experimentation, e.g. an in vivo experiment using a control group.

In embodiments of the disclosure, a method is provided as defined herein, wherein said method is carried out with the aim of improving or maintaining the animal's health.

Hence, in embodiments of the disclosure, methods are provided as defined herein, wherein the animal to be treated is an animal suffering from or at risk of suffering from a condition or pathology. Furthermore, in embodiments of the disclosure, methods are provided as defined herein, for curative and/or prophylactic treatment of a condition or pathology in an animal.

More in particular, in embodiments of the disclosure, methods are provided as defined herein, wherein the animal to be treated is an animal suffering from or at risk of suffering from pathogen infection, preferably intestinal pathogen infection, more preferably caecal and/or colonic pathogen infection. In embodiments of the disclosure, a method is provided as defined herein, for treating and/or preventing pathogen infection, preferably intestinal pathogen infection, more preferably caecal and/or colonic pathogen infection. In accordance with the disclosure, said pathogen may be selected from bacteria, eimeria, viruses and fungi, more preferably said pathogen is selected from bacteria, most preferably from *Clostridium acetobutylicum*, *Escherichia coli*, *Streptococcus cremoris*, *Lactococcus lactis*, *Lactococcus cremoris*, *Clostridium perfringens*, *Campylobacter jejuni*, *Campylobacter coli*, *Lawsonia intracellullaris*, *Brachyspira hyodysenteriae*, *Enterococcus caecorum*, *Streptococcus suis*, *Salmonella enteritidis* and combinations thereof, preferably *Clostridium perfringens*, *Campylobacter jejuni*, *Campylobacter coli*, *Lawsonia intracellullaris*, *Brachyspira hyodysenteriae*, *Enterococcus caecorum*, *Streptococcus suis*, *Salmonella enteritidis* and combinations thereof.

In an embodiment, a method is provided as defined herein, wherein the animal to be treated is an animal suffering from or at risk of suffering from disturbances in the intestinal flora, in particular disturbances in the caecal and/or colonic microflora. In embodiments of the disclosure a method is provided as defined herein for improving the intestinal microflora of an animal and/or for maintaining a healthy intestinal flora in an animal, in particular for improving the caecal and/or colonic microflora and/or for maintaining a healthy caecal and/or colonic microflora. In embodiments of the disclosure, methods as defined herein are provided that result in and/or are aimed at increasing the microbial count of bacteria from the *Lactobacillus* or *Bifidobacterium* genus in the gastro-intestinal tract, preferably the lower gastro-intestinal tract, preferably the caeca or colon. In embodiments of the disclosure, methods as defined herein are provided that result in and/or are aimed at increasing the ratio of microbial counts of bacteria from the *Lactobacillus* or *Bifidobacterium* genus compared to microbial counts of bacteria from the Enterobacteriaceae family in the gastro-intestinal tract, preferably the lower gastro-intestinal tract, preferably the caeca or colon. In embodiments of the disclosure, methods as defined herein are provided that result in and/or aimed at increasing the ratio of microbial counts of bacteria from the *Lactobacillus* or *Bifidobacterium* genus compared to microbial counts of bacteria from the *Salmonella* genus in the gastro-intestinal tract, preferably the lower gastro-intestinal tract, preferably the caeca or colon. In embodiments of the disclosure, methods as defined herein are provided that result in and/or aimed at improving the intestinal microflora comprising increasing the ratio of microbial counts of bacteria from the *Lactobacillus* or *Bifidobacterium* genus compared to microbial counts of bacteria from the *Salmonella* genus in the gastro-intestinal tract, preferably the lower gastro-intestinal tract, preferably the caeca or colon wherein the ratio is approximated by determining the microbial count of one species of bacteria representative of each genus and calculating the ratio using the microbial count of the representative bacteria. In accordance with such embodiments, reducing or increasing the microbial count or ratio of microbial counts should be construed broadly and could for example be understood to mean one or more of the following:

- A reduction or increase in the number of colony forming units (CFU) determined using a suitable method known to the person skilled in the art, measured 1-10, preferably 1-5, preferably 3 days after treatment is started and compared to a group of animals which were not treated,
- A reduction or increase in the number of colony forming units (CFU) determined using a suitable method known to the person skilled in the art, measured in the same animal(s) before treatment and 1-10, preferably 1-5, preferably 3 days after treatment is started, or
- any other method known to the person skilled in the art to determine the effect of feed supplementation with a polysaccharide butyryl ester in accordance with the disclosure.

A further aspect of the present disclosure is directed to uses of the polysaccharide butyryl ester as defined herein and/or the feed grade composition containing said polysaccharide butyryl ester as defined herein, for the methods of treatment as defined here above.

A further aspect of the present disclosure is directed to the use of the polysaccharide butyryl ester as defined herein and/or the feed grade composition containing said polysaccharide butyryl ester as defined herein in the manufacture of a composition for use in the methods of treatment as defined here above.

A further aspect of the present disclosure is directed to the polysaccharide butyryl ester as defined herein and/or the feed grade composition containing said polysaccharide butyryl ester as defined herein, for use in the methods of treatment as defined here above.

A further aspect of the disclosure is directed to the use of the polysaccharide butyryl ester as defined herein as an animal feed component or ingredient.

A further aspect of the disclosure is directed to a method of preparing an animal feed composition as described herein, said method comprising:
  providing a first animal feed component,
  providing a polysaccharide butyrate ester, and
  mixing the first animal feed component with the polysaccharide butyrate ester to a homogeneous blend.

In an embodiment said method comprises:
  providing a first animal feed component,
  providing a polysaccharide butyrate ester,
  mixing the first animal feed component with the polysaccharide butyrate ester to a homogeneous blend, and
  pelletizing the homogeneous blend.

Thus, the disclosure has been described by reference to certain embodiments discussed above. It will be recognized that these embodiments are susceptible to various modifications and alternative forms well known to those of skill in the art. Many modifications in addition to those described above may be made to the structures and techniques described herein without departing from the spirit and scope of the disclosure. Accordingly, although specific embodiments have been described, these are examples only and are not limiting upon the scope of the disclosure. Furthermore, for a proper understanding of this document and in its claims, it is to be understood that the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The following examples are offered for illustrative purposes only, and are not intended to limit the scope of the present disclosure in any way.

EXAMPLES

Example 1: In Vitro Fermentation Assay

In order to assess the capacity of the polysaccharide butyryl esters of the present disclosure to increase the butyrate concentration in the gastro-intestinal tract (GIT) of animals, an in vitro fermentation assay was performed wherein GIT bacteria of broiler chickens were inoculated together with a product in accordance with the disclosure, a positive control and a negative control.

Medium
  1 liter medium consists of 0.6 g KCL, 0.6 g NaCl, 0.2 g CaCl2.2H$_2$O, 0.5 g MgSO$_4$.7H$_2$O, 1.5 g Pipes buffer, 0.54 g NH$_4$Cl, 1.0 g trypticase, 1 ml resazurin solution (0.2 g resazurin per 200 ml distilled water), 10 ml 'Trace Mineral Solution', 12 ml vitamin/phosphate solution, 10 ml Haemin Solution (0.1 g Haemin/1 L distilled water), 4 mg/ml NaHCO$_3$ and 1 mg/ml cysteine HCl.

Trace Mineral Solution
  0.025 g CuCl.2H$_2$O, 0.020 g FeSO$_4$.7H$_2$O, 0.025 ZnCl$_2$, 0.025 g CuCl$_2$.H$_2$O, 0.050 g CoCl$_2$.6H$_2$O, 0.050 g SeO$_2$, 0.250 g NiCl$_2$.6H$_2$O, 0.250 g Na$_2$MoO$_4$.2H$_2$O, 0.0314 g NaVO$_3$, 0.250 H$_3$BO$_3$/1 L 0.02 M HCl dissolution Vitamin/phosphate solution
  0.0204 g biotin, 0.0205 g folic acid, 0.1640 g calcium D-phantothenate, 0.1640 g nicotinamide, 0.1640 riboflavin, 0.1640 g thiamin HCl, 0.1640 g pyridoxine HCl, 0.0204 g para-amino benzoic acid, 0.0205 cyanocobalamin (vitamin B12) per 1 L distilled water containing 54.7 g KH$_2$PO$_4$.

Inoculum
  Intestinal sample of ileum, colon and caecum of the GIT of a 4-week old broiler Ross 408 was collected. Inoculum was prepared the same way for every segment. Immediately after dissection the samples were placed under anaerobic conditions with a temperature of 37° C. (anaerobic chamber, Ruskinn Technology, Bridgend, UK). The content was weighed of every segment and diluted in a ratio of 1:9 with pre-warmed (37° C.) anaerobic, sterile phosphate buffered saline. After homogenization, test products were added and the diluted material was inoculated in a ratio of 1:10 in the above-described medium.

Test Material
  As shown in the below table, three different materials were tested for their capacity to increase the butyrate concentration in the GIT. All tests were performed at 0.5% w/v end concentration.
  A representative polysaccharide butyryl ester in accordance with the disclosure is cellulose acetate butyrate. Xylo-oligosaccharides were included as a positive control because of their known prebiotic effects on butyrate-producing bacteria. In order to assess the effect of the cellulose backbone on the butyrate concentration, a negative control consisting of cellulose was also tested.

| Test | Product | Supplier | Specifications |
|---|---|---|---|
| 1 | Cellulose acetate butyrate (CAB) | Acros Organics ® | 50-54% butyryl content <4% acetyl content |
| 2 | Xylo-oligosaccharides (XOS) | Longlive ® | 35% XOS |
| 3 | Cellulose | Sigma-Aldrich ® | |

Measurement Butyrate Concentration

Fluid samples were collected at timepoints 0 h, 4 h 6 h and 24 h after inoculation for analysis of butyrate concentration with HPLC-UV. Extraction protocol and equipment was used as described by De Baere et al. (Journal of Pharmaceutical and Biomedical Analysis 80 (2013) 107-115.

Results

FIG. 1 shows the butyrate concentrations measured for the ileum inoculum.

Figure 2:
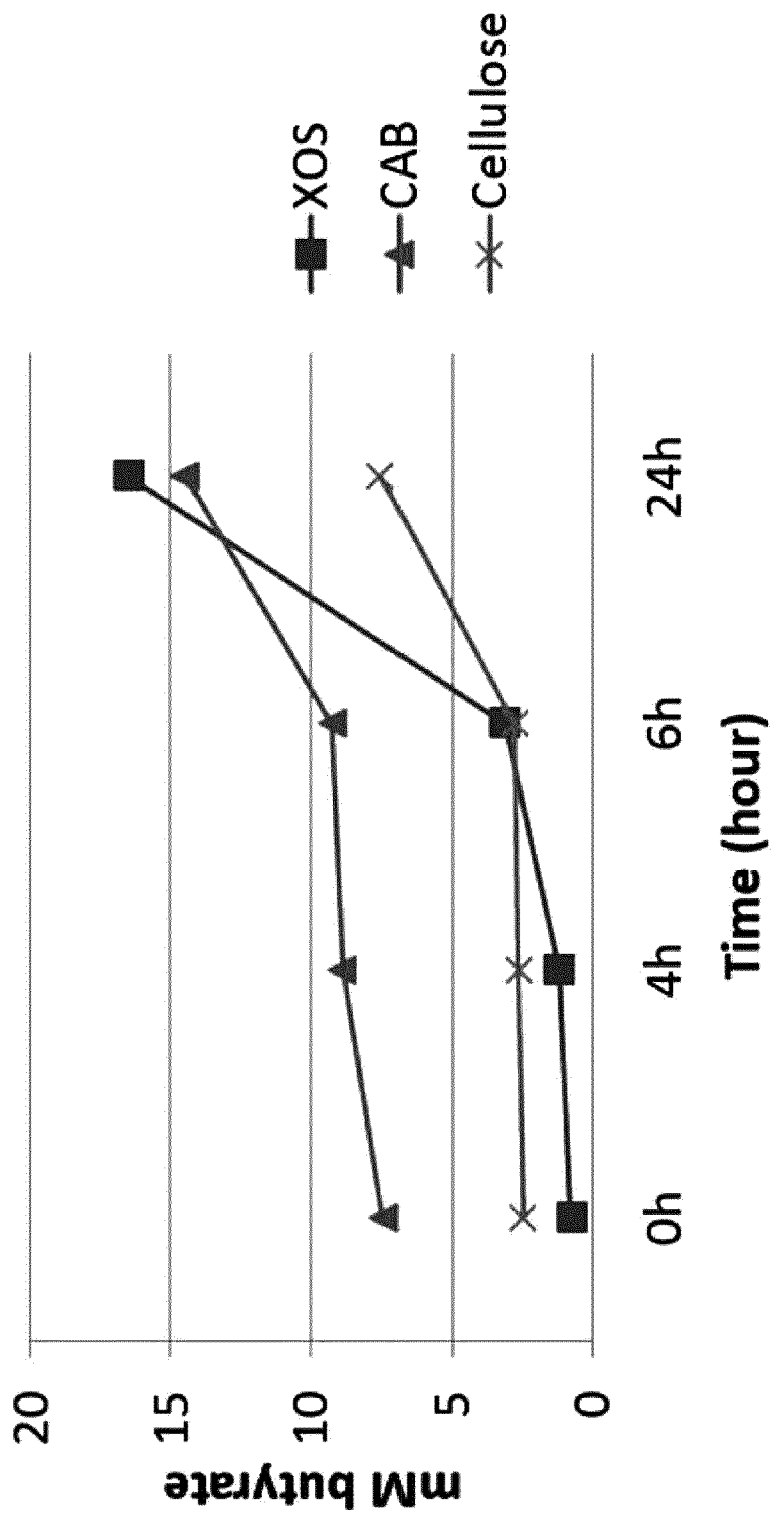
FIG. 2: Butyrate concentrations measured in example 1—Colon inoculum.

FIG. 2 shows the butyrate concentrations measured for the colon inoculum.

Figure 3:
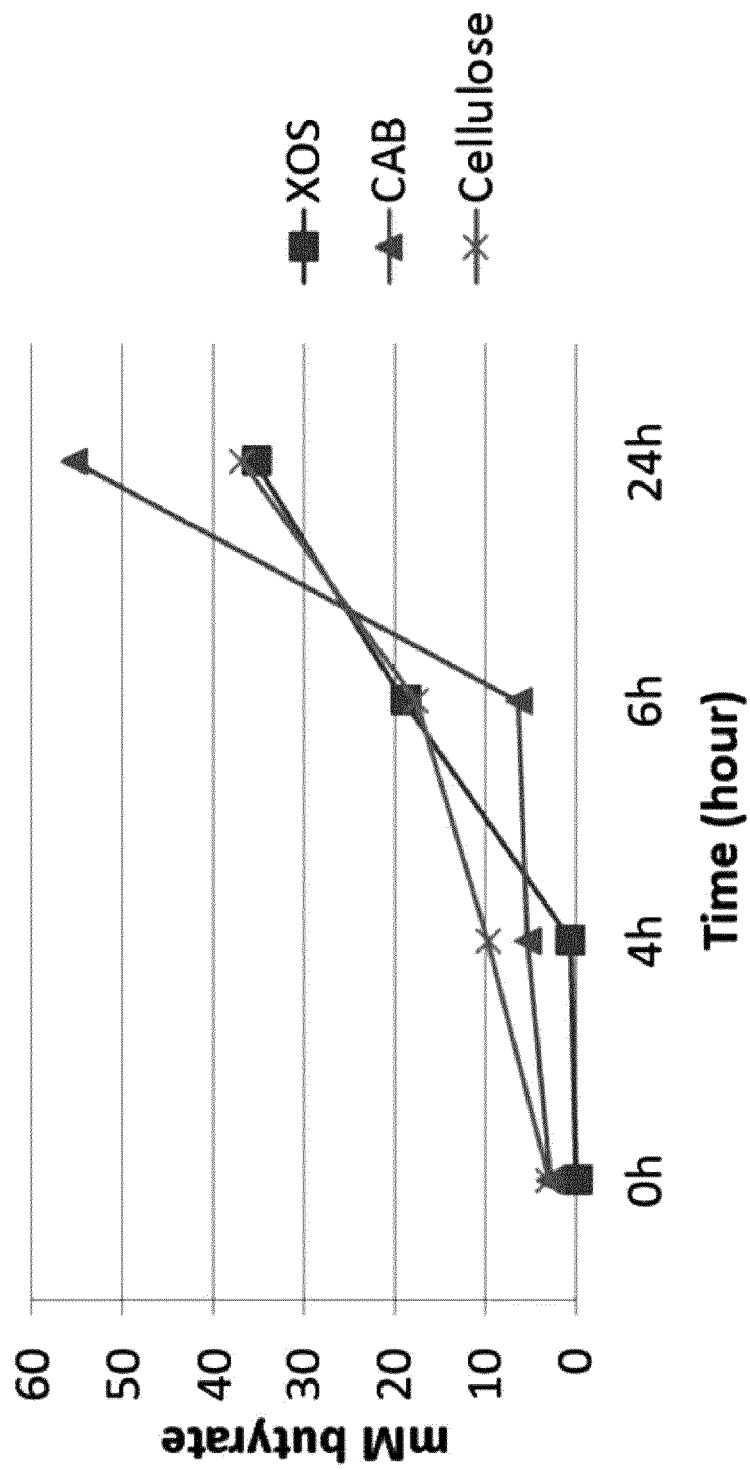
FIG. 3: Butyrate concentrations measured in example 1—Caecum inoculum.

FIG. 3 shows the butyrate concentrations measured for the caecum inoculum.

The results clearly show that CAB is able to increase the butyrate concentration significantly above the butyrate concentration measured for the negative control.

Example 2: In Vivo Determination of Butyrate Concentration in Poultry Colon

In order to assess the capacity of the polysaccharide butyryl esters of the present disclosure to increase the butyrate concentration in the lower gastro-intestinal tract (GIT) of animals, an in vivo experiment was performed. A product in accordance with the disclosure was added to poultry feed, the butyrate concentration in the colon determined and compared to results obtained with other delayed release formulations or products.

Animals

Ross 308 broiler chickens were used in this feed trial. 1-day old chicks were obtained from a commercial hatchery and were kept in isolation. All treatment groups were housed in the same room in separate cages, with litter on the floor. 60 chickens were divided into eight groups of 7 or 8 chickens each (including a blanco group).

Test Feed Compositions

Seven different test feed compositions were prepared by mixing the test products shown in the below table with commercial mash broiler feed (Versele-Laga, Belgium) at a concentration of 3 g sodium butyrate per kg feed. The test feed was subsequently pelletized (without steam) to avoid selective feed intake. The pelletizing technique, pellet size and commercial broiler feed was the same for all test products.

| Test | Product | Supplier | Specifications |
|---|---|---|---|
| 1 | Control - no additive | NA | NA |
| 2 | Adimix 30 Coated ® | Nutri-Ad ® | 30% sodium butyrate coated with palm fat |
| 3 | Polysaccharide butyryl ester:Cellulose acetate butyrate (CAB) | Acros Organics ® | 50-54% butyryl content <4% acetyl content |
| 4 | Polyhydroxybutyrate (Ralstonia) | Metabolix ® | 100% hydroxybutyrate |
| 5 | Wax matrix with 10% starch | Self-prepared | 30% sodium butyrate in Lunacera M ® crystalline matrix and starch. |
| 6 | Tributyrin | Self-prepared | 60% tributyrin (Proviron) on silica (Caldic, Belgium) |
| 7 | Unprotected butyrate (Sodium butyrate) | Nutri-Ad ® | 100% sodium butyrate |

Experimental Set-Up

During the 19th, 20th and 21th days of age, average daily feed intake was measured by pen. Male and female chickens of 22 d of age were randomly assigned to one of the above described test feed compositions and received a restrictive feeding diet (95% of the average intake previously measured) during the 22-27 d period.

At 28 days of age, the birds were sacrificed and the colon collected.

Measurement of Butyrate Concentrations

One gram of intestinal content of the colon of each chicken was weighed and diluted with 1 mL distilled water. After dilution the samples were homogenized and centrifuged at 13.000 rpm for 20 minutes and stored at −20° C. until extraction for HPLC-UV analysis. Extraction protocol and equipment was used as described by De Baere et al. (Journal of Pharmaceutical and Biomedical Analysis 80 (2013) 107-115). For test 4, polyhydroxybutyrate, the hydroxybutyrate concentration was measured and displayed in FIG. 4.

Results

Figure 4:
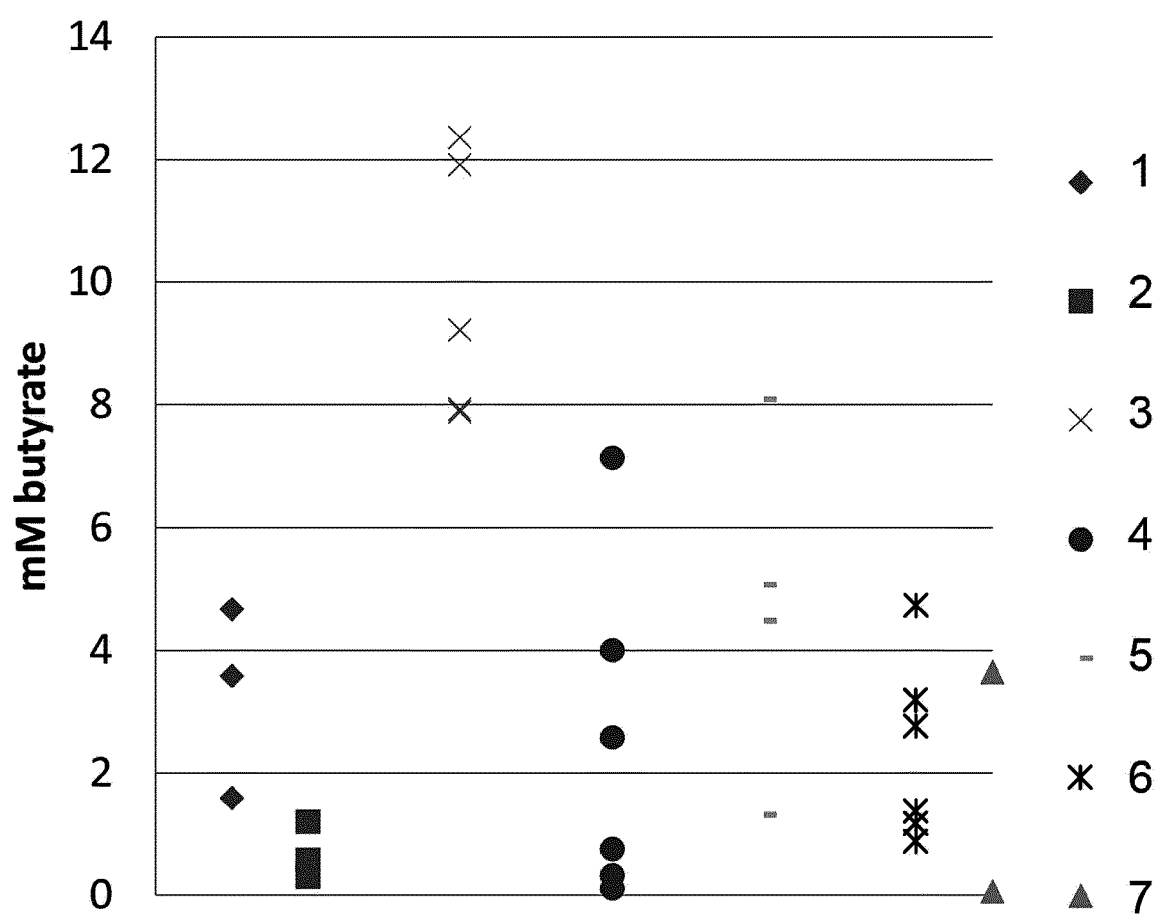
FIG. 4: Butyrate concentrations measured in example 2—Colon.

The results are shown in FIG. 4 as a concentration of butyrate in millimolar (mM)/gram intestinal content plotted per treatment group. If there was not enough intestinal content or the extraction failed, no data was included for that measurement.

The results clearly show that CAB is able to increase the butyrate concentration in the colon significantly above the butyrate concentration measured for the control or other delayed release formulations or products.

Example 3: In Vivo Determination of Post-Infection *Salmonella* Presence in Caeca In order to assess the capacity of the polysaccharide butyryl esters of the present disclosure to decrease *Salmonella* colonization of the gut of animals infected by *Salmonella* Enteritidis, an in vivo experiment was performed. A product in accordance with the disclosure was added to poultry feed, the presence of *Salmonella* Enteritidis in the caecum determined and compared to results obtained with other delayed release butyrate formulations or products.

Animals

Ross 308 broiler chickens were used in this trial. 1-day old chicks were obtained from a commercial hatchery. All treatment groups were housed under the same conditions in separate cages, with litter on the floor. 160 chickens were divided into eight groups of 20 chickens each (including the control group). The four test feed compositions were tested in duplo. All chicks had ad libitum access to water and feed.

Test Feed Compositions

Four different test feed compositions were prepared by mixing the test products shown in the below table with commercial mash broiler feed (Versele-Laga, Belgium) at a concentration of 3 g sodium butyrate per kg feed. The test feed was subsequently pelletized (without steam) to avoid selective feed intake. The pelletizing technique, pellet size and commercial broiler feed was the same for all test products.

| Test | Product | Supplier | Specifications |
|---|---|---|---|
| 1 | Control - no additive | NA | NA |
| 2 | Adimix 30 Coated ® | Nutri-Ad ® | 30% sodium butyrate coated with palm fat |
| 3 | Wax matrix with 10% starch | Self-prepared | 30% sodium butyrate in Lunacera M ® crystalline matrix and starch. |
| 4 | Poylsaccharide butyryl ester:Cellulose acetate butyrate (CAB) | Acros Organics ® | 50-54% butyryl content <4% acetyl content |

*Salmonella* Strain

*Salmonella* Enteritidis strain SE147, a well-characterized streptomycin-resistant strain isolated from a poultry farm (Methner et al., 1995), was used in this experiment. The strain was grown for 6 h in Luria-Bertoni medium (LB, Sigma, St. Louis, Mo.), after which the number of cfu per milligram was determined by plating 10-fold dilutions of the bacterial suspension on xylose lysine deoxycholate agar (XLD, Oxoid, Basingstoke, UK) containing 100 μg/mL of streptomycin (Sigma, St. Louis, Mo.). The bacterial suspension was stored at 4° C. during plate counting and was diluted in PBS to obtain the desired infection dose.

Experimental Set-Up

At 17 days post-hatch all chicks were orally inoculated with $10^5$ cfu of *Salmonella* Enteritidis per bird. At day 4 post infection all birds were euthanized and samples of caecum were taken for bacteriological analysis. The experiment was approved by the ethical committee of the Faculty of Veterinary Medicine, Ghent University.

Bacteriological Analysis

Samples of caeca were homogenized in vol of buffered peptone water (BPW, Oxoid, Basingstoke, UK), and 10-fold dilutions were made in PBS. For each dilution, 6×20 μL was inoculated on XLD plates containing 100 μg/mL streptomycin. After an overnight incubation at 37° C., the number of cfu per gram of tissue was determined. Samples that were negative after direct plating were preenriched overnight at 37° C. in buffered peptone water (BPW, Oxoid, Basingstoke, UK), after which all samples were enriched by addition of 1 mL of this suspension to 9 mL of brilliant green tetrathionate broth (Oxoid, Basingstoke, UK). Samples that were *Salmonella* negative after titration but positive after enrichment were assumed to contain $1×10^1$ cfu/g of tissue. Samples that were still negative after enrichment were assumed to have 0 cfu/g of tissue.

Results

As shown in the table below, administration of feed comprising a polysaccharide butyryl ester such as CAB provides significantly improved results with regard to *Salmonella* colonization of the caeca compared to other delayed release formulations or products.

| *Salmonella* presence | Control | 2 | 3 | 4 |
|---|---|---|---|---|
| Negative | 0 | 0 | 0 | 0 |
| Positive after enrichment | 6 | 14 | 13 | 27 |
| $10^2 < x < 10^3$ cfu/g | 12 | 8 | 7 | 4 |
| $10^3 < x < 10^4$ cfu/g | 6 | 14 | 5 | 8 |
| $>10^4$ cfu/g | 15 | 4 | 15 | 1 |

Example 4: In Vivo Determination of Post-Infection *Salmonella* Presence in Cloacal Swabs In order to assess the capacity of the polysaccharide butyryl esters of the present disclosure to decrease *Salmonella* fecal shedding of animals infected by *Salmonella* Enteritidis, an in vivo experiment was performed. A product in accordance with the disclosure was added to poultry feed, the presence of *Salmonella* Enteritidis in cloacal swabs determined and compared to results obtained with other delayed release butyrate formulations or products.

Animals

Ross 308 broiler chickens were used in this trial. 1-day old chicks were obtained from a commercial hatchery. All treatment groups were housed under the same conditions in separate cages, with litter on the floor. 80 chickens were divided into four groups of 20 chickens each (including the control group). The four test feed compositions listed below were tested. All chicks had ad libitum access to water and feed.

Test Feed Compositions

Four different test feed compositions were prepared by mixing the test products shown in the below table with commercial mash broiler feed (Versele-Laga, Belgium) at a concentration of 3 g sodium butyrate per kg feed. The test feed was subsequently pelletized (without steam) to avoid selective feed intake. The pelletizing technique, pellet size and commercial broiler feed was the same for all test products.

| Test | Product | Supplier | Specifications |
|---|---|---|---|
| 1 | Control - no additive | NA | NA |
| 2 | Adimix 30 Coated ® | Nutri-Ad ® | 30% sodium butyrate coated with palm fat |
| 3 | Wax matrix with 10% starch | Self-prepared | 30% sodium butyrate in Lunacera M ® crystalline matrix and starch. |
| 4 | Polsaccharide butyryl ester:Cellulose acetate butyrate (CAB) | Acros Organics ® | 50-54% butyryl content <4% acetyl content |

*Salmonella* Strain

*Salmonella* Enteritidis strain SE147, a well-characterized streptomycin-resistant strain isolated from a poultry farm (Methner et al., 1995), was used in this experiment. The strain was grown for 6 h in Luria-Bertoni medium (LB, Sigma, St. Louis, Mo.), after which the number of cfu per milligram was determined by plating 10-fold dilutions of the bacterial suspension on xylose lysine deoxycholate agar (XLD, Oxoid, Basingstoke, UK) containing 100 μg/mL of streptomycin (Sigma, St. Louis, Mo.). The bacterial suspension was stored at 4° C. during plate counting and was diluted in PBS to obtain the desired infection dose.

Experimental Set-Up

At 17 days post-hatch all chicks were orally inoculated with $10^5$ cfu of *Salmonella* Enteritidis per bird. At day −1, 1 and 3 post infection, cloacal swabs were taken for bacteriological analysis. The experiment was approved by the ethical committee of the Faculty of Veterinary Medicine, Ghent University.

Bacteriological Analysis

Cloacal swabs were plated on XLD plates containing 100 μg/mL of streptomycin and incubated overnight at 37° C. Samples that were negative after direct plating were preenriched overnight at 37° C. in buffered peptone water (BPW, Oxoid, Basingstoke, UK), after which the samples were enriched by addition of 1 mL of this suspension to 9 mL of brilliant green tetrathionate broth (Oxoid, Basingstoke, UK). This suspension was again incubated overnight at 37° C., and afterwards plated on XLD containing 100 μg/mL of streptomycin. After an overnight incubation at 37° C., the number of cfu per cloacal swab was determined. Samples that were *Salmonella* negative after titration but positive after enrichment were marked as positive for *Salmonella* presence. Samples that were still negative after enrichment were marked as negative for *Salmonella* presence.

Results

As shown in the table below, administration of feed comprising a polysaccharide butyryl ester such as CAB provides significantly improved results with regard to fecal shedding of *Salmonella* compared to other delayed release formulations or products.

| Days past infection | *Salmonella* presence | Control | 2 | 3 | 4 |
|---|---|---|---|---|---|
| −1 | Negative | 20 | 20 | 20 | 20 |
|  | Positive | 0 | 0 | 0 | 0 |
| 1 | Negative | 5 | 14 | 17 | 16 |
|  | Positive | 15 | 6 | 3 | 4 |
| 3 | Negative | 5 | 14 | 13 | 17 |
|  | Positive | 15 | 6 | 7 | 3 |

Example 5: In Vivo Determination of Growth Performance

In order to assess the capacity of the polysaccharide butyryl esters of the present disclosure to influence the growth performance under suboptimal farming practices, an in vivo experiment was performed. A product in accordance with the disclosure was added to a challenging rapeseed meal (RSM) diet, the effects on growth performance determined and compared to results obtained with other delayed release butyrate formulations or products.

Experimental Design

The experiment was designed as a complete randomized block design. Treatment groups were arranged as a 3×2 factorial plus control with 3 delayed release butyrate formulations or products and two supplementation levels (0.25 or 1 g butyrate/kg feed as fed basis). Each treatment group was replicated six times, resulting in a total of six blocks. Diets were based on a RSM-Corn-Wheat starter, grower and finisher diets detailed in the below tables. Experimental starter and grower diets were derived from the basal recipe by adding the feed additives at the expense of soybean oil.

|  | Product | Supplier | Specifications |
|---|---|---|---|
| 1 | Control - no additive | NA | NA |
| 2 | Adimix 30 Coated ® | Nutri-Ad ® | 30% sodium butyrate coated with palm fat |
| 3 | Wax matrix | Self-prepared | 30% sodium butyrate in Lunacera M ® crystalline matrix. |
| 4 | Polsaccharide butyryl ester:Cellulose acetate butyrate (CAB) | Acros Organics ® | 50-54% butyryl content <4% acetyl content |

Starter Composition

| Ingredient | 1-CTR | 2-H | 2-L | 3-H | 3-L | 4-H | 4-L |
|---|---|---|---|---|---|---|---|
| Corn | 295.96 | 295.96 | 295.96 | 295.96 | 295.96 | 295.96 | 295.96 |
| Wheat | 200 | 200 | 200 | 200 | 200 | 200 | 200 |
| Rapeseedmeal | 350 | 350 | 350 | 350 | 350 | 350 | 350 |
| Fishmeal | 75 | 75 | 75 | 75 | 75 | 75 | 75 |
| Soybean oil | 55.29 | 51.96 | 54.46 | 51.96 | 54.46 | 53.29 | 54.79 |
| Premix | 5 | 5 | 5 | 5 | 5 | 5 | 5 |
| Lime fine | 9 | 9 | 9 | 9 | 9 | 9 | 9 |
| Monocalcium phosphate | 5.5 | 5.5 | 5.5 | 5.5 | 5.5 | 5.5 | 5.5 |
| Salt | 0.9 | 0.9 | 0.9 | 0.9 | 0.9 | 0.9 | 0.9 |
| NaHCO3 | 2.8 | 2.8 | 2.8 | 2.8 | 2.8 | 2.8 | 2.8 |
| L-Lysine HCl | 0.5 | 0.5 | 0.5 | 0.5 | 0.5 | 0.5 | 0.5 |
| Natuphos 1000G | 0.05 | 0.05 | 0.05 | 0.05 | 0.05 | 0.05 | 0.05 |
| Adimix 30 Coated ® | 0 | 3.33 | 0.83 | 0 | 0 | 0 | 0 |
| Wax matrix | 0 | 0 | 0 | 3.33 | 0.83 | 0 | 0 |
| CAB | 0 | 0 | 0 | 0 | 0 | 2 | 0.5 |
| Total | 1000 | 1000 | 1000 | 1000 | 1000 | 1000 | 1000 |

Grower Composition

| Ingredient | 1-CTR | 2-H | 2-L | 3-H | 3-L | 4-H | 4-L |
|---|---|---|---|---|---|---|---|
| Corn | 215.35 | 215.35 | 215.35 | 215.35 | 215.35 | 215.35 | 215.35 |
| Wheat | 300 | 300 | 300 | 300 | 300 | 300 | 300 |
| Rapeseedmeal | 350 | 350 | 350 | 350 | 350 | 350 | 350 |

-continued

|                | Item |      |      |      |      |      |      |
|----------------|------|------|------|------|------|------|------|
| Ingredient     | 1-CTR | 2-H | 2-L | 3-H | 3-L | 4-H | 4-L |
| Fishmeal       | 55   | 55   | 55   | 55   | 55   | 55   | 55   |
| Soybean oil    | 63.00 | 59.67 | 62.17 | 59.67 | 62.17 | 61.00 | 62.50 |
| Premix         | 5    | 5    | 5    | 5    | 5    | 5    | 5    |
| Lime fine      | 8    | 8    | 8    | 8    | 8    | 8    | 8    |
| Salt           | 1.2  | 1.2  | 1.2  | 1.2  | 1.2  | 1.2  | 1.2  |
| NaHCO3         | 1.4  | 1.4  | 1.4  | 1.4  | 1.4  | 1.4  | 1.4  |
| L-Lysine HCl   | 1    | 1    | 1    | 1    | 1    | 1    | 1    |
| Natuphos 1000G | 0.05 | 0.05 | 0.05 | 0.05 | 0.05 | 0.05 | 0.05 |
| Adimix 30 Coated ® | 0 | 3.33 | 0.83 | 0 | 0 | 0 | 0 |
| Wax matrix     | 0    | 0    | 0    | 3.33 | 0.83 | 0    | 0    |
| CAB            | 0    | 0    | 0    | 0    | 0    | 2    | 0.5  |
| Total          | 1000 | 1000 | 1000 | 1000 | 1000 | 1000 | 1000 |

Finisher Composition

|                      | Item   |
|----------------------|--------|
| Ingredient           | 1-CTR  |
| Corn                 | 229.35 |
| Wheat                | 300    |
| Rapeseedmeal         | 350    |
| Fishmeal             | 40     |
| Soybean oil          | 64.00  |
| Premix               | 5      |
| Lime fine            | 7.5    |
| Salt                 | 1.2    |
| NaHCO3               | 1.4    |
| L-Lysine HCl         | 1.5    |
| Natuphos 1000G       | 0.05   |
| Fat-coated butyrate  | 0      |
| Wax-coated butyrate  | 0      |
| CAB                  | 0      |
| Total                | 1000   |

The premix provided per kg of diet: vitamin A, 12.000 IU; vitamin D3, 2.500 IU; vitamin E, 50 mg; vitamin B2, 7.5 mg; vitamin B6, 3.5 mg; vitamin B1, 2.0 mg; vitamin K3, 1.5 mg; vitamin B12, 20 µg; choline chloride, 460 mg; antioxidant (oxytrap PXN), 125 mg; niacin, 35 mg; pantothenic acid, 12 mg; biotin, 0.2 mg; folic acid, 1 mg; Mn, 85 mg; Fe, 80 mg; Zn, 60 mg; Cu, 12 mg; I, 0.8 mg; Se, 0.15 mg.

Starter diets were fed from d 0 till d 21, grower diets from d 22 till d 35 and finisher diet was fed from d 36 till slaughter at d 42. Diets were formulated to meet or exceed the requirements of broiler chickens and were produced by Research Diet Services (Wijk bij Duurstede, The Netherlands).

Birds and Experimental Procedures

The experiment was conducted at the research farm Carus of Wageningen University. A total of 357 male one-day-old broilers (initial BW 47 g; Ross 308, Aviagen Group, Newbridge, United Kingdom) were obtained from a commercial hatchery (Morren Breeders B.V., Lunteren, the Netherlands). Upon arrival, birds were individually weighed and assigned to a weighed category (Small<µ−0.68×σ; µ−0.68× σ<Medium<µ+0.68×σ; Large>µ+0.68×σ). Birds of each category were randomly assigned to one of the 42 floor pen of two climate-controlled rooms. Each pen housed 8 to 9 birds, had a dimension of 1.85×1 m (L×W) and was enriched with a perch. Wood shavings were used as a bedding material. Ambient temperature was maintained at 32° C. until d 3 and thereafter gradually reduced to 22° C. at d 23. A 23 L:1 D photoperiod was applied until d 3 and was changed thereafter to 16 L:8 D. Birds were allowed ad libitum access to feed and water. Pen bodyweights as well as pen feed intake were recorded at d 21, 35 and 42. Mortality was monitored on a daily basis and body weight of dead birds was recorded.

Results

The tables below show the feed conversion ratio (FCR), average bodyweight gain (ADG) and average daily feed intake (ADFI) and mortality rate. FCR was calculated at pen level using ADG and ADFI. Results were also recalculated as percentage of change relative to their respective control.

The tables below show the mortality, average daily weight gain (ADG), average daily food intake (ADFI) and feed conversion ratio (FCR) results obtained in this experiment. The data shows that feed supplementation with a polysaccharide butyryl ester such as CAB provides superior growth performance results compared to other delayed release butyrate formulations or products. The polysaccharide butyryl ester in accordance with the present disclosure provides the highly desirable combination of improved ADG and ADFI combined with decreased FCR and mortality during the supplementation period without showing adverse effects during the finisher period.

The results also show that in the starter and grower phase, increasing inclusion of the polysaccharide butyryl ester (4-L vs. 4-H) leads to increased performance (in contrast to the effect observed for the wax compositions 3-L vs. 3-H).

Effect of Dietary Treatments on Performance Parameters During the Starter, Grower and Finisher Periods.

|             | Dietary treatment | | | | | | |
|-------------|-----|-----|-----|-----|-----|-----|-----|
|             | 1   | 2   |     | 3   |     | 4   |     |
| Item        | CTR | L   | H   | L   | H   | L   | H   |
|             | 0-21 d | | | | | | |
| Mortality, %| 5.9 | 2.0 | 0.0 | 0.0 | 0.0 | 0.0 | 0.0 |
| ADG, g/bird | 39.9 | 39.7 | 42.0 | 41.8 | 40.4 | 40.6 | 41.4 |

-continued

|  | Dietary treatment | | | | | | |
|---|---|---|---|---|---|---|---|
|  | 1 | 2 | | 3 | | 4 | |
| Item | CTR | L | H | L | H | L | H |
| ADFI, g/bird | 54.5 | 53.8 | 56.7 | 56.6 | 54.2 | 55.3 | 56.9 |
| FCR, g:g | 1.37 | 1.36 | 1.35 | 1.35 | 1.34 | 1.36 | 1.38 |
| | | | 22-35 d | | | | |
| Mortality, % | 0.0 | 0.0 | 3.9 | 3.9 | 2.0 | 0.0 | 0.0 |
| ADG, g/bird | 89.8 | 90.8 | 90.5 | 89.4 | 87.6 | 93.8 | 96.4 |
| ADFI, g/bird | 140.3 | 139.9 | 154.0 | 147.0 | 139.0 | 141.0 | 146.3 |
| FCR, g:g | 1.58 | 1.55 | 1.73 | 1.65 | 1.59 | 1.51 | 1.52 |
| | | | 35-42 d | | | | |
| Mortality, % | 4.2 | 0.0 | 0.0 | 2.0 | 4.0 | 0.0 | 2.0 |
| ADG, g/bird | 131.9 | 107.3 | 125.0 | 120.3 | 116.4 | 115.7 | 116.9 |
| ADFI, g/bird | 224.1 | 197.6 | 211.5 | 198.6 | 214.7 | 213.0 | 211.2 |
| FCR, g:g | 1.71 | 1.85 | 1.71 | 1.66 | 1.84 | 1.85 | 1.81 |

Effect of Dietary Treatments on Performance Parameters During the Supplementation and Total Experimental Periods.

|  | Dietary treatment | | | | | | |
|---|---|---|---|---|---|---|---|
|  | 1 | 2 | | 3 | | 4 | |
| Item | CTR | L | H | L | H | L | H |
| | Supplementation period (0-35 d) | | | | | | |
| Mortality, % | 7.8 | 2.0 | 3.9 | 5.9 | 3.9 | 0.0 | 0.0 |
| ADG, g/bird | 59.51 | 60 | 61.3 | 60.8 | 59.1 | 61.9 | 63.4 |
| ADFI, g/bird | 88.26 | 88 | 95.5 | 92.5 | 87.8 | 89.6 | 92.7 |
| FCR, g:g | 1.49 | 1.47 | 1.56 | 1.53 | 1.49 | 1.45 | 1.46 |
| | Total experiment (0-42 d) | | | | | | |
| Mortality, % | 9.8 | 2.0 | 3.9 | 5.9 | 5.9 | 0.0 | 2.0 |
| ADG, g/bird | 70.42 | 67.9 | 71.6 | 70.3 | 68.4 | 70.9 | 72.3 |
| ADFI, g/bird | 108.9 | 106 | 114 | 110 | 108 | 110 | 112 |
| FCR, g:g | 1.55 | 1.57 | 1.60 | 1.56 | 1.58 | 1.56 | 1.56 |

Effect of Dietary Treatments on the Performance Parameters Recalculated as Percentage of Change Relative to their Respective Control During the Supplementation Period (0-35 d)

|  | 2 | | 3 | | 4 | |
|---|---|---|---|---|---|---|
|  | L | H | L | H | L | H |
| ADG, % change | 0.9 | 3.0 | 2.0 | −0.7 | 3.8 | 6.1 |
| ADFI, % change | −0.3 | 7.6 | 4.6 | −0.6 | 1.5 | 4.7 |
| FCR, % change | −1.4 | 4.8 | 2.3 | −0.2 | −2.7 | −1.8 |

Example 6: In Vivo Determination of Feed Conversion Rate

In order to assess the capacity of the polysaccharide butyryl esters of the present disclosure to influence the feed conversion rate under suboptimal farming practices, an in vivo experiment was performed. A product in accordance with the disclosure was added to a challenging rapeseed meal (RSM) diet, the effects on feed conversion rate determined, statistically analyzed and compared to results obtained with other delayed release (hydroxy)butyrate formulations or products.

Experimental Design

The experiment was designed as a complete randomized block design. Treatment groups were arranged as 10 birds/pen×8 replicates×4 treatments: a control and 3 delayed release butyrate formulations or products (at 1 g (hydroxy)butyrate/kg feed). Diets were based on a RSM-Corn-Wheat starter and grower diets detailed in the below tables. Experimental starter and grower diets were derived from the basal recipe by adding the feed additives at the expense of soybean oil.

|  | Product | Supplier | Specifications |
|---|---|---|---|
| 1 | Control - no additive | NA | NA |
| 2 | Adimix 30 Coated ® | Nutri-Ad ® | 30% sodium butyrate coated with palm fat |
| 3 | Polyhydroxybutyrate (PHB) | Nutri-Ad ® | 0.10% butyrate biomass |
| 4 | Polysaccharide butyryl ester:Cellulose acetate butyrate (CAB) | Fisher-Scientific, Waltham, USA | 50-54% butyryl content <4% acetyl content |

Starter Composition

|  | Item | | | |
| --- | --- | --- | --- | --- |
| Ingredient | 1-CTR | 2 | 3 | 4 |
| Corn | 296 | 296 | 296 | 296 |
| Wheat | 200 | 200 | 200 | 200 |
| Rapeseedmeal | 350 | 350 | 350 | 350 |
| Fishmeal | 75 | 75 | 75 | 75 |
| Soybean oil | 55.3 | 52.0 | 54.3 | 53.5 |
| Premix | 5 | 5 | 5 | 5 |
| Lime fine | 9 | 9 | 9 | 9 |
| Monocalcium phosphate | 5.5 | 5.5 | 5.5 | 5.5 |
| Salt | 0.9 | 0.9 | 0.9 | 0.9 |
| NaHCO3 | 2.8 | 2.8 | 2.8 | 2.8 |
| L-Lysine HCl | 0.5 | 0.5 | 0.5 | 0.5 |
| Natuphos 1000G | 0.05 | 0.05 | 0.05 | 0.05 |
| Adimix 30 Coated ® | 0 | 3.33 | 0 | 0 |
| PHB | 0 | 0 | 1 | 0 |
| CAB | 0 | 0 | 0 | 1.8 |
| Total | 1000 | 1000 | 1000 | 1000 |

Grower Composition

|  | Item | | | |
| --- | --- | --- | --- | --- |
| Ingredient | 1-CTR | 2 | 3 | 4 |
| Corn | 215.4 | 215.4 | 215.4 | 215.4 |
| Wheat | 300.0 | 300.0 | 300.0 | 300.0 |
| Rapeseedmeal | 350.0 | 350.0 | 350.0 | 350.0 |
| Fishmeal | 55.0 | 55.0 | 55.0 | 55.0 |
| Soybean oil | 63.0 | 59.7 | 62.0 | 61.2 |
| Premix | 5 | 5 | 5 | 5 |
| Lime fine | 8 | 8 | 8 | 8 |
| Monocalcium phosphate | — | — | — | — |
| Salt | 1.2 | 1.2 | 1.2 | 1.2 |
| NaHCO3 | 1.4 | 1.4 | 1.4 | 1.4 |
| L-Lysine HCl | 1 | 1 | 1 | 1 |
| Natuphos 1000G | 0.05 | 0.05 | 0.05 | 0.05 |
| Adimix 30 Coated ® | 0 | 3.33 | 0.00 | 0 |
| PHB | 0 | 0 | 1 | 0 |
| CAB | 0 | 0 | 0 | 1.8 |
| Total | 1000 | 1000 | 1000 | 1000 |

The premix provided per kg of diet: vitamin A, 12.000 IU; vitamin D3, 2.500 IU; vitamin E, 50 mg; vitamin B2, 7.5 mg; vitamin B6, 3.5 mg; vitamin B1, 2.0 mg; vitamin K3, 1.5 mg; vitamin B12, 20 µg; choline chloride, 460 mg; antioxidant (oxytrap PXN), 125 mg; niacin, 35 mg; pantothenic acid, 12 mg; biotin, 0.2 mg; folic acid, 1 mg; Mn, 85 mg; Fe, 80 mg; Zn, 60 mg; Cu, 12 mg; I, 0.8 mg; Se, 0.15 mg.

Starter diets were fed from d 0 till d 21 and grower diets from d 22 till d 35. Diets were formulated to meet or exceed the requirements of broiler chickens and were produced by Research Diet Services (Wijk bij Duurstede, The Netherlands).

Birds and Experimental Procedures

The experiment was conducted at the experimental poultry house 12 of the ILVO-DIER, (Burg, Merelbeke, BE). A total of 320 male one-day-old broilers (Ross 308, Aviagen Group, Newbridge, United Kingdom) were obtained from a commercial hatchery (Belgabroed NV, Merksplas, BE). Upon arrival, birds were randomly assigned to one of the 32 floor pens of a single climate-controlled room. Each pen housed 10 birds and had a dimension of 2.1×1 m. Ambient temperature was maintained at 29-30° C. until d 7 and thereafter reduced by 2° C. per week. A 23 L:1 D photoperiod was applied until d 7 and was changed thereafter to 16 L:8 D. Birds were allowed ad libitum access to feed and water. Individual and pen body weights, as well as pen feed intake, were recorded every week.

Statistical Analysis

Performance parameters were analysed using the PROC GLM of SAS (version 9.3, SAS Institute Inc., Cary, N.C.) using the following model $$Y_{ijk}=\mu+D_i+W_j+B_k+AW_{ij}+\varepsilon_{ijk}$$

where $Y_{ijk}$ is the observed response of the $k^{th}$ replicate (k=1 to 8) of the fed the $i^{th}$ diet (i=CTR, FCB, PHB, CAB) during the $j^{th}$ week (j=1 to 5), $D_i$ is the $i^{th}$ fixed diet effect, $B_k$ is the $k^{th}$ fixed block effect, $W_j$ is the $j^{th}$ random effect of measurement period, and $AD_{ij}$ the interaction effect between the diet and measurement period, and $\varepsilon_{ijk}$ is the residual error term of the $k^{th}$ replicate fed the $i^{th}$ diet at the $j^{th}$ measurement period. When a significant diet effect was detected, means were separated using Tukey post-hoc test. When a significant interaction between diet and measurement period was detected, means were separated using Tukey post-hoc test and the interaction term was partitioned per week by a simple effect test.

Results

Effects of dietary butyrate supplementation on the feed conversion ratio (FCR) over the 0-35 d supplementation period are shown in the table below.

The data shows that feed supplementation with a polysaccharide butyryl ester such as CAB provides superior feed conversion ratio results compared to other delayed release butyrate formulations or products. The feed conversion ratio improvement for CAB was statistically significant.

Effect of Dietary Butyrate Supplementation on the Growth Performance During the Entire 0-35 d Period

|  | Treatment group | | | | Pooled | p-value | | | |
| --- | --- | --- | --- | --- | --- | --- | --- | --- | --- |
| Item | 1-CTR | 2 | 3 | 4 | SEM | Diet | Week | Block | Diet*Week |
| BWG | 48.41 | 48.26 | 48.36 | 48.56 | 1.62 | 0.9981 | <.0001 | 0.2511 | 0.0032 |
| VFI | 79.15 | 76.52 | 77.42 | 76.08 | 1.93 | 0.6898 | <.0001 | 0.5882 | 0.5192 |
| FCR | 1.64 | 1.59 | 1.60 | 1.57 | 0.02 | 0.0164 | <.0001 | 0.7997 | 0.0194 |

The invention claimed is:
1. A non-therapeutic method for
decreasing the feed conversion ratio,
increasing the life weight, or
increasing the average daily weight gain,
in livestock animals that are in good or normal health, said method comprising the step of administering in admixture with the animal feed, a cellulose butyryl ester which further comprises acetyl ester groups, wherein the cellulose butyryl ester includes a number average molar mass of 2000-1000000 g/mol,
wherein said cellulose butyryl ester has an acetyl content selected from at least 1 wt % and at most 10 wt %.

2. The non-therapeutic method according to claim 1, wherein the average number of butyryl groups per monosaccharide unit is within the range of 0.1-4.

3. The non-therapeutic method of claim 1, wherein the cellulose butyryl ester is administered in the inhibition or treatment of pathogen infection, wherein pathogen is selected from one or more of bacteria, eimeria, viruses, and fungi.

4. The non-therapeutic method according to claim 1, wherein the animal to be administered is a poultry species.

5. The non-therapeutic method of claim 1, wherein said cellulose butyryl ester has an acetyl content of at least 2%.

6. The non therapeutic method of claim 1, wherein said cellulose butyryl ester has an acetyl content of at most 8%.

* * * * *